(12) United States Patent
Lindsay et al.

(10) Patent No.: US 7,665,460 B2
(45) Date of Patent: Feb. 23, 2010

(54) MICRO POWERED GAS-FORMING DEVICE

(75) Inventors: Jeffrey D. Lindsay, Appleton, WI (US);
Fung-Jou Chen, Appleton, WI (US);
Carl G. Rippl, Appleton, WI (US);
David J. Tyrrell, Decatur, GA (US);
Kim Ellefson, Oshkosh, WI (US); Mary Jo Meyer, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 722 days.

(21) Appl. No.: 11/247,917

(22) Filed: Oct. 11, 2005

(65) Prior Publication Data

US 2007/0079889 A1    Apr. 12, 2007

(51) Int. Cl.
*A61M 11/00*    (2006.01)
(52) U.S. Cl. .......................... 128/200.14; 128/200.16; 128/200.18
(58) Field of Classification Search ............ 128/200.14, 128/200.16, 200.17, 203.15, 200.18, 203.12
See application file for complete search history.

(56) References Cited

U.S. PATENT DOCUMENTS

| | | | |
|---|---|---|---|
| 3,796,186 A | 3/1974 | Bounds et al. | |
| 3,828,773 A * | 8/1974 | Buch et al. ............. | 128/200.16 |
| 4,541,132 A | 9/1985 | Long | |
| 4,549,243 A | 10/1985 | Owen et al. | |
| 4,561,037 A | 12/1985 | MacLaine et al. | |
| 4,649,895 A | 3/1987 | Yasuki et al. | |
| 4,663,639 A | 5/1987 | Owen et al. | |
| 4,965,977 A | 10/1990 | White | |
| 5,121,884 A | 6/1992 | Noakes | |
| 5,184,778 A | 2/1993 | Noakes | |
| 5,186,164 A * | 2/1993 | Raghuprasad .......... | 128/200.14 |
| 5,222,664 A | 6/1993 | Noakes et al. | |
| 5,251,416 A | 10/1993 | White | |
| 5,553,607 A | 9/1996 | Chiu et al. | |
| 5,626,936 A | 5/1997 | Alderman | |
| 5,631,099 A | 5/1997 | Hockaday | |
| 5,810,265 A | 9/1998 | Cornelius et al. | |
| 5,895,418 A | 4/1999 | Saringer | |
| 5,921,232 A * | 7/1999 | Yokoi et al. ............ | 128/200.14 |
| 5,927,618 A | 7/1999 | Jefferies et al. | |
| 5,932,011 A | 8/1999 | Noakes et al. | |

(Continued)

FOREIGN PATENT DOCUMENTS

EP    1081780 A2    3/2001

(Continued)

OTHER PUBLICATIONS

English language abstract of Japanese Patent No. JP54058954, published May 12, 1979.

(Continued)

*Primary Examiner*—Steven O Douglas
(74) *Attorney, Agent, or Firm*—Dority & Manning, P.A.

(57) ABSTRACT

A gas dispenser includes a reservoir for holding a liquid, and a chamber in communication with the reservoir. The chamber receives the liquid, and a micro power source generates energy for conversion of the liquid disposed in the chamber. A nozzle defining an orifice in selective communication with the chamber. The nozzle is used to release the converted liquid from the chamber through the orifice.

46 Claims, 8 Drawing Sheets

U.S. PATENT DOCUMENTS

| | | |
|---|---|---|
| 5,932,940 A | 8/1999 | Epstein et al. |
| 6,079,634 A | 6/2000 | Noakes et al. |
| 6,138,671 A | 10/2000 | Noakes et al. |
| 6,311,903 B1 | 11/2001 | Gaw et al. |
| 6,318,647 B1 | 11/2001 | Gaw et al. |
| 6,326,097 B1 * | 12/2001 | Hockaday .................... 429/34 |
| 6,376,444 B1 | 4/2002 | Hortel et al. |
| 6,392,313 B1 | 5/2002 | Epstein et al. |
| 6,517,648 B1 | 2/2003 | Bouchette et al. |
| 6,541,149 B1 | 4/2003 | Maynard et al. |
| 6,589,294 B2 | 7/2003 | Hortel et al. |
| 6,653,005 B1 | 11/2003 | Muradov |
| 6,689,466 B2 | 2/2004 | Hartmann |
| 6,703,127 B2 | 3/2004 | Davis et al. |
| 6,802,875 B1 | 10/2004 | Kimbara et al. |
| 6,861,169 B2 | 3/2005 | Hagan et al. |
| 6,864,010 B1 | 3/2005 | McLean |
| 2001/0029911 A1 | 10/2001 | Yang et al. |
| 2002/0061954 A1 | 5/2002 | Davis et al. |
| 2002/0172846 A1 | 11/2002 | Hagan et al. |
| 2003/0053643 A1 | 3/2003 | Bank et al. |
| 2003/0091502 A1 | 5/2003 | Holladay et al. |
| 2003/0167689 A1 | 9/2003 | Hsu |
| 2004/0072039 A1 | 4/2004 | Jankowski et al. |
| 2004/0211189 A1 | 10/2004 | Arnold |
| 2004/0223908 A1 | 11/2004 | Holladay et al. |
| 2005/0003249 A1 | 1/2005 | Hsu |
| 2005/0008907 A1 | 1/2005 | Isozaki et al. |
| 2005/0016550 A1 | 1/2005 | Katase |
| 2005/0150489 A1 * | 7/2005 | Dunfield et al. ........ 128/200.14 |
| 2005/0171466 A1 | 8/2005 | Diemunsch |

FOREIGN PATENT DOCUMENTS

| | | |
|---|---|---|
| EP | 1113518 A1 | 7/2001 |
| EP | 1099269 B1 | 3/2004 |
| FR | 2127956 A | 10/1972 |
| GB | 352351 A2 | 7/1931 |
| JP | 54058954 | 5/1979 |
| WO | WO 9711503 | 3/1997 |
| WO | WO 9944254 | 9/1999 |
| WO | WO 0029535 | 5/2000 |
| WO | WO 02 091508 A2 | 11/2002 |
| WO | WO 03 040618 A2 | 5/2003 |
| WO | WO 03 078895 A1 | 9/2003 |
| WO | WO 2004 004052 A2 | 1/2004 |
| WO | 2004011071 A1 | 2/2004 |
| WO | WO 2004 083036 A1 | 9/2004 |
| WO | WO 2004 094906 A2 | 11/2004 |
| WO | 2004105846 A2 | 12/2004 |

OTHER PUBLICATIONS

Printed Advertisement for Vapor Shot™ Personal Vaporizer from www.vaporshot.com.

Pacific Northwest National Library paper entitled "Microheater" ca. Jul. 21, 1999, by Drost et al.

International Search Report from related PCT application mailed Sep. 14, 2006.

* cited by examiner

MICRO POWERED GAS-FORMING DEVICE

BACKGROUND OF THE INVENTION

Consumers use a variety of devices to produce vapor and steam for breathing comfort and for cleaning purposes. Vaporizers, for instance, deliver vapor in low humidity environments to prevent dry skin and sinus passages and also to deliver therapeutic or medicinal ingredients such as menthol and pharmaceutical agents. Steamers provide steam for cleaning clothes, curtains and the like. However, vaporizers and steamers using conventional power generation components such as batteries and electrical power cords suffer from a number of drawbacks. If battery power is used, the batteries tend to deplete rapidly and must be replaced regularly, which over time becomes expensive. If conventional electrical power is chosen, electrical cords prevent portability of the vaporizer or steamer.

A device is needed in the industry, which utilizes a compact, portable power source that enables a user to transport the vaporizer or steamer in a purse, pocket, suitcase or the like, and which can be quickly and economically recharged without the expense, environmental issues and other limitations associated with conventional batteries.

BRIEF SUMMARY OF THE INVENTION

The present invention generally provides a micro powered gas-forming device such as a vaporizer and a steamer. A micro power source facilitates portability of the gas-forming device by eliminating electrical power cords in some embodiments and bulky motors in other embodiments while providing direct heat generation or electrical power in the gas-forming device with the energy being obtained from the reaction of a fuel with oxygen. The component parts of the micro powered gas-forming device are simple and economical to manufacture, assemble and use. Other advantages of the invention will be apparent from the following description and the attached drawings, or can be learned through practice of the invention.

As used herein, the term "fluid" means a liquid or a gas.

As used herein, the term "gas" means a vapor, steam, aerosol, smoke, fog or mist produced by a vaporizer, nebulizer, atomizer, steamer or the like, and can include a suspension of fine, solid or liquid particles.

As used herein, the term "solution" means a liquid comprising a solvent and one or more solutes and can be aqueous or nonaqueous. The solution can include water, various active ingredients such as medications, fragrance additives or agents and the like.

As used herein, the term "regulator" means a valve, switch or trigger used to release an aerosol, vapor or steam.

As used herein, the term "controller" means a control element or device or a control assembly used to activate a resistor, an electrostatic charger or other electrically powered device.

As used herein, the term "micro power sources" are devices that convert a fuel (typically a liquid such as methanol) into energy via a reaction with oxygen either by electrochemical routes to produce electricity for resistive heating or by chemical routes (e.g., combustion or direct oxidation) to release thermal energy. Micropower sources can include any type of micro-fuel cell, micro-gas turbine (micro engine), micro-heater or their combinations, which may, for example, deliver 10 to 100 times as much energy as conventional lithium ion batteries occupying the same volume. For instance, the micro power sources may deliver power to devices of the present invention from about 0.2 Watts (W) to 2000 W, more particularly from about 0.5 W to about 200 W.

The micropower source need not produce electricity, but, some versions of the invention may be other power sources capable of generating thermal energy from a fuel, and also capable of user control to turn on or shut off power production at will, unlike, for example, iron-based exothermic reaction systems used in commercial hand warming pads and other products. In some embodiments described herein, the user can also adjust a setting to control the rate at which energy is produced from the fuel. If the energy is heat, a workpiece can be heated directly. If the energy produced is electricity, the electricity can be used for resistive heating or to activate the workpiece. Of course, when electricity is produced, a portion of the energy produced by the fuel will be released as waste heat, which can be captured and utilized in various aspects of the invention.

Further, the "micro power sources" according to various aspects of the present invention can be readily rechargeable by simply adding fuel to an empty fuel cartridge or replacing a spent fuel cartridge as will be described in detail in the following discussion.

More specifically, the micro-fuel cells according to various embodiments described herein are devices that electrochemically oxidize a fuel to generate electricity. Exemplary methods of coupling micro-fuel cells with portable electrical devices are described and shown, for example but without limitation, in U.S. Pat. No. 6,326,097 to Hockaday, which is incorporated herein by reference.

The micro-gas turbines contemplated in various embodiments herein generally include a miniature compressor that compresses incoming air to high pressure, a combustion area that burns the fuel and produces high-pressure, high-velocity gas, and a tiny turbine that extracts the energy from the high-pressure, high-velocity gas flowing from the combustion chamber, which is then converted to electricity. Examples of microturbines that convert fuel to electricity are found in U.S. Pat. No. 5,932,940 to Epstein et al. and U.S. Pat. No. 6,392,313 to Epstein et al., which are incorporated herein by reference without limitation.

The microheater used in various embodiments described herein is a microscale heating system that can be used for personal or portable heating and cooling devices. The microheater has the capability of producing up to 30 W of thermal energy per square centimeter of external combustor area and can heat a portable heater, for instance, for as long as eight hours on minimal fuel. Exemplary microheater applications are described by Drost et al. in a Pacific Northwest National Laboratory paper entitled *MicroHeater*, ca. Jul. 21, 1999, which is incorporated herein and without limitation by reference thereto.

Another example of fuel cell technology, which can be used in various embodiments of the present invention is a hydrogen-based fuel cell system, which is available for instance but without limitation from Angstrom Power Solutions (North Vancouver, British Columbia, Canada). Such a system is described, for example, in U.S. Pat. No. 6,864,010, to McLean, which is incorporated by reference. The hydrogen-based fuel cell system uses compressed hydrogen gas in cartridges or metal hydride storage systems. A proton exchange membrane with a porous diffusion material and catalyst generates electricity from the reaction of oxygen and hydrogen, with an optional hybrid battery connected to the fuel cell. The fuel cell can be cylindrical, as in the shape of existing AA lithium batteries, or can have a prismatic shape. For example, an Angstrom V50 cylindrical fuel cell is 2.6 cosmetic in diameter and 2 cm long, producing 1 W at 5 volts.

A V60 fuel cell is a prismatic fuel cell with dimensions of 5 mm×27 mm×19 mm. As presented at the 7th Annual Small Fuel Cell 2005 Conference, Washington, D.C., Apr. 27-29, 2005, Angstrom fuel cells may deliver energy of 700 Whr/liter or 170 Whr/kg at 50% net efficiency.

In various embodiments of the present invention, the gas-forming device comprises a container, reservoir of liquid such as water or an aqueous solution disposed within the container, a micropower source associated with the container for converting fuel into thermal energy (either directly or by electric heating from electricity produce from the fuel), means for applying the thermal energy to vaporize a portion of the liquid to produce steam (e.g., a conductive plate, heating rods, or a resistive heater in communication with the micropower source positioned to deliver energy therefrom into the liquid), control means to allow a user to control the delivery of energy from the micropower source (e.g., an on-off switch or a variable heating level dial), and a nozzle attached to the container for delivering the vaporized liquid to a user for inhalation or other treatments.

The device can take many forms and can be portable. For example, it may resemble a cup or mug of liquid but with a nozzle at its top to provide a directed, gentle flow of steam. It may be in the form of a pendant suspended on a chain or string that can be worn around the neck, with the gas-forming device suspended below the head of the user and with a nozzle delivering steam upward toward the mouth and nose. It can be substantially in the form of a box or cube that can be carried and positioned stably on a table or other surface. It can be in the form of headgear (e.g., in the style of headphones or earmuffs) with a tube to deliver steam in front of the face.

With particular reference to the micro-fuel cell form of a micro power source, the micro-fuel cell generates and delivers electrical power to the devices very efficiently. The micro-fuel cell can be but is not limited to a polymer electrolyte membrane (PEM) cell, a direct methanol cell (DMFC—a form of PEMFC discussed below), a phosphoric acid cell, an alkaline cell, a molten carbonate cell, a solid oxide cell, and a regenerative (reversible) micro-fuel cell. Other types of micro-fuel cells may include small MEMS (micro electrical machined system) devices, which are also suitable for electrical power applications. The MEMS-based fuel cell can be a solid oxide type (SOFC), a solid polymer type (SPFC), or a proton exchange membrane type (PEMFC). Each MEMS micro-fuel cell can have an anode and a cathode separated by an electrolyte layer. Additionally, catalyst layers can also separate the electrodes (cathode and anode) from the electrolyte as discussed below.

By way of more specific example, the PEM micro-fuel cells use a membrane to separate the fuel from the oxygen. A catalyst such as platinum may be present on, in, or otherwise associated with the membrane to help generate hydrogen ions from the fuel in the presence of an electrochemical circuit that receives an electron as a hydrogen ion is generated. The membrane, typically wetted with water, allows hydrogen ions from the fuel to diffuse toward the oxygen where it reacts electrochemically. The overall reactions involved may be, in the case of methanol fuel cell:

The flow of electrons across the circuit occurs at a voltage that can be used to conduct useful work; i.e., to power cleaning devices as described herein.

By way of further example but not of limitation, a micro-fuel cell in another aspect of the invention can be made from two silicon substrates. Porous silicon is formed along the surface of the substrate in a desired pattern provided by a mask. Suitable mask materials include those that do not dissolve in HF, e.g., silicon nitride, gold and chromium. Ambient mask conditions are next changed to provide electropolishing to form gas delivery tunnels or channels underlying the porous regions. A variety of patterns are suitable for these tunnels or channels such as serpentine, parallel, wheel and spoke or fractal patterns. The mask provides a final structure in which the porous silicon regions are supported, typically by portions of the mask itself. The resulting structure provides porous silicon regions formed in the surface of the substrate, with underlying tunnel regions formed within the substrate.

In this exemplary micro-fuel cell, two silicon current collector/gas diffusion structures are prepared as described above. A catalyst layer is then formed on each silicon structure (on the surface in which the porous silicon regions are formed) for both electrodes. The catalyst layer is formed by any suitable technique, e.g., sputtering or spinning an emulsion of catalyst particles. The catalyst layer can be, for example, platinum or platinum/carbon (e.g., carbon particles having attached platinum particles). Additionally, a platinum/ruthenium catalyst is useful for reacting with methanol fuel, although the Pt—Ru is generally only used for the catalyst layer in contact with the fuel, with a different catalyst used on the oxidant side of the cell. The catalyst layer is electrically conductive (i.e., at least 1 ohm$^{-1}$cm$^{-1}$) and is in electrical contact with the silicon current collector.

On one of the foregoing substrates, a proton exchange membrane is formed on the catalyst layer. As used herein, the term "proton exchange membrane" indicates any suitable material that allows ions to conduct across it. Forming the proton exchange membrane encompasses in situ techniques such as spin or solution casting, as well as providing a preformed film onto the catalyst. An exemplary membrane for use in this construction is the Nafion® brand membrane sold by the Dupont® company. Specifically, the Nafion® brand membrane is a perfluorosulfuric acid membrane with a polytetrafluoroethylene backbone.

Those skilled in the art will appreciate that other films are commercially available and suitable for use as the membrane. For example but not by way of limitation, modified Nafion® brand membranes can be obtained by treatment with electron beams or chemical modification (e.g., addition of a polybenzimidazole layer applied with screen printing or other printing techniques). The membrane can also contain exfoliated clays or hydrocarbons.

The selected membrane is next formed on the catalyst layer by liquid phase techniques, e.g., spin casting or solution casting, or by assembly of a pre-cast film. The membrane thickness ranges from about 10 to about 50 μm. In the case of a pre-cast film, the catalyst material is generally painted onto the film, e.g., as an ink containing the catalyst, alcohols, and the membrane polymer.

It should be understood that there is no well-defined boundary between the catalyst layer and the membrane. For example, in the case of spin or solution casting, the catalyst layer surface generally has some texture, and casting of the membrane layer on such a textured surface causes the ionically conducting polymer to move into such textured regions, e.g., into local valleys of the catalyst layer. Painting a catalyst material onto a pre-cast membrane provides a similar result.

To finish forming the micro-fuel cell, one of the above-described electrode structures is placed on the other electrode structure such that the catalyst layer of the second substrate contacts the proton exchange membrane. Generally, a PTFE or solubilized form of the proton exchange membrane is used to bond the catalyst layer to the membrane, followed by a heat treatment to drive off alcohol and solvents.

As constructed above, the micro-fuel cell operates as follows: fuel, e.g., hydrogen or methanol, is introduced into the first current collector (the anode) by directing the fuel through the tunnels such that it diffuses through the porous gas-diffusion regions to the catalyst layer. The catalyst layer promotes formation of hydrogen ions from the fuel, releasing electrons. The electrons flow from the catalyst layer through the anode current collector and through an external circuit, while the hydrogen ions (i.e., protons) move across the membrane toward the second catalyst layer (the cathode catalyst).

In this micro-fuel cell, an oxidant, e.g., air or oxygen, is directed into the tunnels of the cathode current collector, and diffuses through the gas-diffusion porous regions to the second catalyst layer. At this second catalyst layer, oxygen from the oxidant reacts both with the hydrogen ions flowing across the membrane and with the electrons flowing to the catalyst layer from the external circuit to form water. As noted above, this electron flow provides the desired current, and the water by-product is removed from the cell.

With reference now to the direct methanol fuel (DMFC) cell briefly introduced above, an exemplary DMFC cell includes a 13 W fuel cell operating at 15V that can operate for about 10 hours on approximately 100 ml of fuel. Another exemplary DMFC is thumb-sized: about 22 mm×about 56 mm×about 4.5 mm with 1.6 g of methanol fuel in its tank and has an overall mass of about 8.5 g. This micro-fuel cell provides about 20 hours of power at 100 mW for operation of, for example, a heating device using just 2 cc of fuel.

By way of further example, an active micro-fuel cell can provide 1 W of power for about 20 hours with approximately 25 cc of fuel. With the 25 cc methanol fuel cartridge in place, its weight is only about 130 g, with a size of about 100 mm×about 60 mm×about 30 mm (about 140 cc volume). This is equivalent to 6 lithium-ion batteries (3.7V and 600 mAh) that are currently used, for instance, in cellular phones.

By way of further example, Los Alamos National Laboratory (LANL) at Los Alamos, N. Mex. has developed micro-fuel cells such as a 100 $cm^2$ fuel cell for the U.S. Department of Energy and a 19.6 $cm^2$ fuel cell (250 g, 340 W/kg, 25 W nominal and 75-85 W peak power).

Many of the foregoing exemplary micro-fuel cells can use a variety of fuels, e.g., ethyl alcohol, methanol, formic acid, butane, or other fuel sources to produce electrical power. The skilled artisan will instantly recognize that the fuels need not be methanol or other volatile fuels, but can also be non-volatile borohydride—alkaline solutions combined with alcohols such as those provided by Medis Technologies of New York City, N.Y.

A variety of solid oxide fuel cells (SOFCs) can also be used as the micro-fuel cells. In an SOFC, a solid oxide electrolyte is used in combination with a compatible anode and a cathode material. Such an SOFC generates electricity and heat by directly converting the chemical energy of a fuel (hydrogen, hydrocarbons) with an oxidant ($O^2$, air) via an electrochemical process. The SOFC makes use of the property of certain solid-state oxide electrolytes to support a current of oxygen anions; for example, stabilized zirconia or related oxygen-ion conductors.

Also in the SOFC, the electrolyte membrane separates the fuel and oxidant with the cathode side in contact with the oxidant and the anode side in contact with the fuel. Oxygen from the oxidant stream is reduced to $O^{2-}$ anions at the cathode. These anions are transported through the solid electrolyte to the anode side of the cell. At the anode, the $O^{2-}$ ions are reacted with the fuel stream thus releasing electrons to flow back to the cathode. A secondary device in accordance with certain aspects of the present invention can be inserted into the circuit between the anode and cathode to draw useful work from the flow of electrons generated.

In addition to the above-described micro-fuel cells, other fuel cell technologies are suitable for use in various embodiments of the present invention. For example, a methanol fuel cell is available from CMR Fuel Cells, Ltd. of Harston, Cambridge, United Kingdom, which does not require the flow plates used by some fuel cells (compare SOFC above) to keep the fuel and the oxygen separated; i.e., the CMR fuel cell allows operation with mixed fuel and oxygen. Yet other suppliers of micro-fuel cells include Smart Fuel Cell GmbH of Germany, Samsung of South Korea and Microcell of Raleigh, N.C. In particular, the Microcell-PE methanol fuel cells are useful for powering portable devices requiring sub-watt to 100 W power.

In light of the above exemplary micro power sources, according to a particular aspect of the invention, a gas dispenser includes a reservoir configured to hold a liquid; a chamber in communication with the reservoir, the chamber being configured to receive the liquid; a micro power source being configured to generate energy for conversion of the liquid disposed in the chamber to a gas; and a nozzle defining an orifice therethrough in selective communication with the chamber, the nozzle being configured for releasing the gas from the chamber through the orifice. In this aspect, the liquid can be a quantity of water, a quantity of medicine, a quantity of fragrance and combinations of these.

Also in this aspect, the micro power source can generate about 0.2 W to about 200 W. The micro power source can include a fuel cell having a fuel cartridge and a combustion chamber, the fuel cartridge being configured to hold a supply of fuel, the combustion chamber being configured to receive and combust the fuel to generate the energy. The supply of fuel can generate an electrochemical reaction to generate the energy. The fuel cartridge in this aspect can be refillable with a replacement supply of fuel and/or the fuel cartridge can be a replaceable fuel cartridge.

Moreover, the micro power source in this aspect of the invention can be a microturbine engine including a plurality of diffuser vanes and a plurality of compressor blades, the plurality of compressor blades being configured for rotation about the diffuser vanes to generate the energy.

Further, in this aspect the gas dispenser can include an actuator connected to the reservoir for controlling a quantity of the liquid delivered to the chamber. The quantity of the liquid delivered to the chamber can be a dose of medicine.

Also in this aspect, the gas dispenser can include a controller in communication with the micro power source, the controller being configured to activate the micro power source to generate the energy. The controller can be a conductivity contact configured to activate the micro power source by a user touch.

The gas dispenser can further include an electrical device in communication with the micro power source, the electrical device disposed proximate the chamber and configured for converting the liquid to the gas. The electrical device can be a heating element for heating the liquid into the gas. Additionally, or alternatively, the electrical device can be an electrostatic charger for generating electrostatically charged droplets from the liquid.

Also in this aspect of the invention, the gas dispenser can include a regulator interposed between the chamber and the orifice, the regulator being configured to release the gas from the chamber through the orifice.

The gas dispenser can further include a membrane having a plurality of holes in it, the membrane disposed proximate the chamber, the holes being configured to convert at least a portion of the liquid into an aerosol for release through the orifice.

In another aspect of the invention, a gas dispenser can include a first reservoir being configured to hold a first liquid; a second reservoir being configured to hold a second liquid; a chamber in communication with the first and the second reservoirs, the chamber being configured to receive the first and the second liquids; a micro power source being configured to generate energy for conversion of at least one of the first and the second liquids disposed in the chamber into a gas; and a nozzle defining an orifice therethrough in selective communication with the chamber, the nozzle being configured for releasing the gas from the chamber through the orifice. The first liquid in this aspect can be a quantity of water, a quantity of fragrance and combinations of these and other liquids and consumer products. Similarly, the second liquid can be a quantity of water, a quantity of fragrance, a quantity of cleaning solution, a quantity of wax and combinations of these and other consumer products.

Also in this aspect of the invention, the micro power source can generate about 0.2 W to about 200 W. The micro power source can include a microturbine engine being configured to generate the energy and/or include a fuel cell having a fuel cartridge and a combustion chamber, the fuel cartridge being configured to hold a supply of fuel, the combustion chamber being configured to receive and combust the fuel to generate the energy. The supply of fuel can generate an electrochemical reaction to generate the energy. In this aspect, the fuel cartridge can be refillable with a replacement supply of fuel and/or be a replaceable fuel cartridge.

The gas dispenser in this aspect can also include a controller in communication with the micro power source, the controller being configured to activate the micro power source to generate the energy. The controller can be a conductivity contact being configured to activate the micro power source by a user touch.

Also in this aspect, the gas dispenser can include an electrical device in communication with the micro power source, the electrical device disposed proximate the chamber and configured for converting at least one of the first and the second liquids into the gas. The electrical device can a heating element. Additionally, or alternatively, the electrical device can be an electrostatic charger, the electrostatic charger being configured to generate electrostatically charged droplets from at least one of the first and the second liquids.

Further, in this aspect the gas dispenser can have a regulator interposed between the chamber and the orifice, the regulator being configured to release the gas from the chamber through the orifice.

In yet another aspect of the invention, a gas dispenser can include a reservoir being configured to hold a liquid; a chamber in communication with the reservoir, the chamber being configured to receive a quantity of the liquid; an actuator connected to the reservoir for dosing the quantity of the liquid to the chamber; a micro power source being configured to generate energy for conversion of the liquid disposed in the chamber into an aerosol; and a nozzle defining an orifice therein, the nozzle in selective communication with the chamber, the nozzle being configured for releasing the aerosol from the chamber through the orifice. The liquid can be a quantity of water, a quantity of medicine, a quantity of flavorant and combinations thereof.

In this aspect, the micro power source can generate about 0.2 W to about 200 W. The micro power source can include a fuel cell having a fuel cartridge and a combustion chamber, the fuel cartridge being configured to hold a supply of fuel, the combustion chamber being configured to receive and combust the fuel to generate the energy. The supply of fuel can be adapted for generating an electrochemical reaction to generate the energy. The fuel cartridge can be refillable with a replacement supply of fuel and/or be a replaceable fuel cartridge.

Also in this aspect, the gas dispenser can include a controller in communication with the micro power source, the controller being configured to activate the micro power source to generate the energy. The controller can be a conductivity contact being configured to activate the micro power source by a user touch.

Further, in this aspect of the invention, the gas dispenser can further include an electrical device in communication with the micro power source, the electrical device disposed proximate the chamber and configured for converting the liquid into the aerosol. The electrical device can be a heating element, the heating element being configured to convert at least a portion of the aerosol into steam. Additionally, or alternatively, the electrical device can be an electrostatic charger, the electrostatic charger being configured to generate electrostatically charged droplets in the aerosol.

Also in this aspect, the gas dispenser can include a regulator interposed between the chamber and the orifice, the regulator being configured to release the gas from the chamber through the orifice.

The gas dispenser can also include a membrane defining a plurality of holes therethrough, the membrane disposed proximate the chamber, the holes being configured to convert at least a portion of the liquid into the aerosol for release through the orifice.

Further in this aspect, the gas dispenser can include a mouthpiece disposed proximate the orifice, the mouthpiece being configured for a user to inhale the aerosol from the orifice into a mouth of the user. The mouthpiece can be in the form of a mask configured to be placed over a face and mouth of the user to inhale the aerosol.

Other aspects and advantages of the invention will be apparent from the following description and the attached drawings, or can be learned through practice of the invention.

BRIEF DESCRIPTION OF THE DRAWINGS

The above and other aspects of the present invention will be apparent from the detailed description below and in combination with the drawings in which.

DETAILED DESCRIPTION OF THE INVENTION

Detailed reference will now be made to the drawings in which examples embodying the present invention are shown. The detailed description uses numerical and letter designations to refer to features of the drawings. Like or similar designations in the drawings and description have been used to refer to like or similar parts of the invention.

The drawings and detailed description provide a full and detailed written description of the invention and the manner and process of making and using it, so as to enable one skilled in the pertinent art to make and use it. The drawings and detailed description also provide the best mode of carrying out the invention. However, the examples set forth in the drawings and detailed description are provided by way of explanation of the invention and are not meant as limitations of the invention. The present invention thus includes any modifications and variations of the following examples as come within the scope of the appended claims and their equivalents.

As broadly embodied in the figures, a gas-forming device employing a micro power source is provided. The gas-forming device is used to produce steam or an aerosol for breathing comfort or cleaning. The skilled artisan will instantly recognize that the gas-forming device and its components including materials, combinations and dimensions, which are described in detail below, are modifiable to accommodate various breathing and cleaning requirements and are not limited to only those examples shown in the figures.

Figure 1:
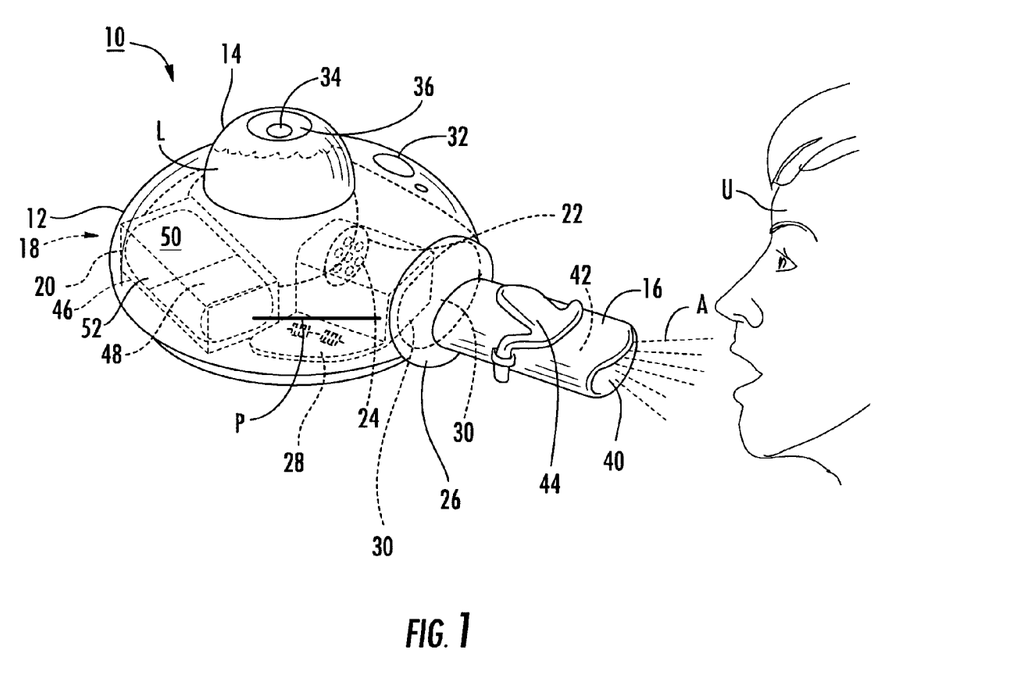
FIG. 1 is a top perspective view of a vaporizer powered by a micro power source according to one embodiment of the invention.
Figure 2:
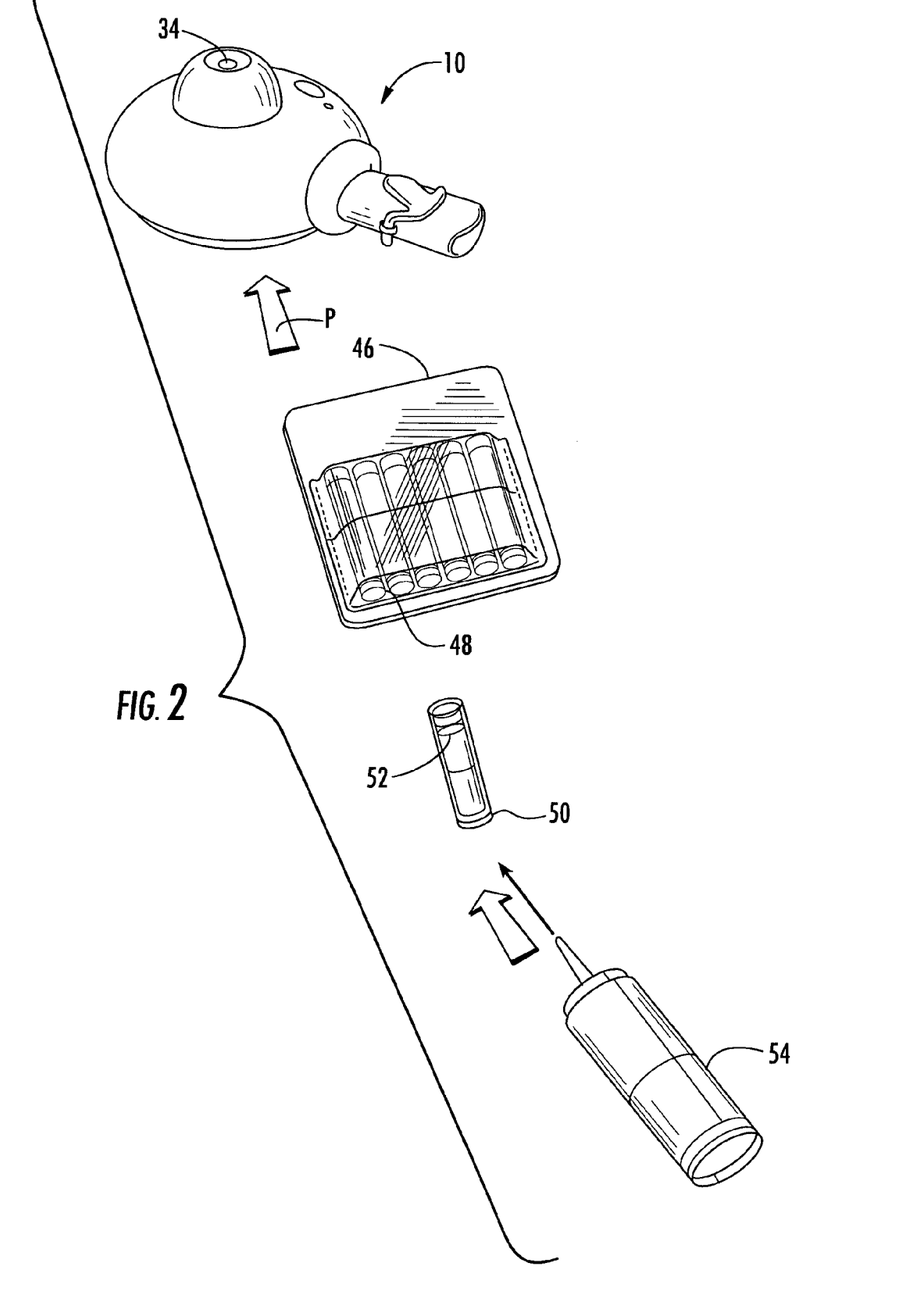
FIG. 2 is an exploded view of a reusable micro power source being inserted in a nebulizer according to an aspect of the invention.

With reference now to FIG. 1, a first embodiment of a nebulizer is designated in general by the element number 10. The nebulizer 10 (alternatively referred to as vaporizer, nebulizer, atomizer or steamer) includes a body or housing 12, a reservoir 14, a delivery portion 16 and a micro power source 18. The micro power source 18 in this aspect of the invention includes a microfuel cell 46, which has a combustion or reaction chamber 48 and a fuel cartridge 50 for storing a quantity of fuel 52. The fuel cartridge 50 may be disposed at a higher elevation than the reaction chamber 48 during normal use in order to permit gravitational feed of the fuel to the reaction chamber 48, if desired, although micro pumps, capillary pressure, or other methods may be used to deliver the fuel in other embodiments. Further details of the microfuel cell 46, its components and operation are provided in detail below.

As shown in FIG. 1, the housing 12 of the nebulizer 10 includes a compartment 20 for housing the microfuel cell 46 or other micropower devices. In this aspect of the invention, a membrane 22 is located in the body 12 between the reservoir 14 and an aerosol chamber 26. As shown, the membrane 22 has a plurality of holes 24 for generating an aerosol A and the aerosol chamber 26 is formed in the housing 12 for receiving a liquid L held in the reservoir 14. As the liquid L is forced through the holes 24 of the membrane 22, the liquid L is converted to the aerosol A, which is released through an orifice 40 of the delivery portion 16. The delivery portion 16 can be a mask or a mouthpiece through which a user U inhales the aerosol A. For instance, the orifice 40 can be small enough to place in a mouth of the user U, or the orifice 40 can be sufficiently large to place over the mouth as the mask.

FIG. 1 further shows that the housing 12 includes a controller 28, which is connected to an electrical device 30 such as a grid or resistor. As shown, an actuator 34 is depressed or otherwise actuated by the user U to activate the fuel cell 46. As described in greater detail below, the activated fuel cell 46 produces an electrical current, which is sent to the electrical device 30 via the controller 28. The electrical device 30 acts as a load or resistor in this electrical circuit to heat the liquid L as the liquid L is being converted to the aerosol A. The skilled artisan will instantly recognize that the electrical device 30 is not limited to the resistor. For instance, the electrical device 30 can be an electrostatic charger for electrostatically charging the aerosol A. Similarly, the skilled artisan will recognize that the actuator 34 can be a flap valve, a ball valve, a Strater valve or the like for releasing the liquid L and delivering it through the holes 24 of the membrane 22 into the aerosol chamber 26. Moreover, those skilled in the art will recognize that the membrane 22 can be connected electrically to the controller 28 and made to vibrate as the liquid L is forced through the holes 24 to facilitate conversion of the liquid L into the aerosol A.

FIG. 1 further shows a hinged or screw-type cap 36 located around the reservoir 14 for refilling the reservoir 14 with the liquid L as the liquid L is depleted. As briefly introduced, the liquid L can be water or any liquid medication, saline solution or other breathable particulate, which is to be converted by the membrane 22 and/or the resistor 30 into the aerosol A including in gaseous form for inhalation by the user U for medicinal treatment or breathing comfort purposes.

More particularly, as noted above, a first end 38 of the delivery portion 16 is in open communication with the aerosol chamber 26. The orifice 40 defines a second end of the delivery portion 16. As shown, the orifice 40 is inserted in a mouth M of the user U. A passageway 42 interconnects the first end 38 to the orifice 40 for delivery of the aerosol A into the mouth M. Also shown, a valve 44, such as a one-way flap valve to prevent leakage, will open as the user U draws a breath. Alternatively, or in addition to the mechanical one-way flap valve, the valve 44 can be made to open momentarily upon depression of the actuator 34.

Turning now to FIG. 2, the microfuel cell 46 is shown most clearly. In this aspect of the invention, the microfuel cell 46 includes the combustion chamber 48 and the fuel cartridge 50 briefly introduced with respect to FIG. 1 above. As shown, the fuel cartridge 50 holds the fuel 52, which upon activation of the actuator 34, for instance, will deliver the fuel 52 into the combustion chamber 48 for combustion. More particularly, the fuel 52 undergoes an electrochemical reaction in this aspect of the invention in which electrons are transferred in a manner to create the electricity as described in greater detail with respect to FIG. 3 below. The electricity is delivered to the various components such as the electrical device 30 described above via an electrical conduit such as a power line P shown schematically in FIG. 2. As further shown, the fuel cartridge 50 can be refilled with a subsequent quantity of fuel 52 using a refueling device 54, or the fuel cartridge 50 can be removed from the chamber 48 and replaced with a new fuel cartridge after the fuel 52 is depleted from the original fuel cartridge 50.

With reference to FIG. 3, an alternative embodiment of a microfuel cell 146 is shown, which can power a nebulizer 110 similar to the nebulizer 10 discussed above, or a steamer 210 or a steam cleaner 310 as will be described respectively with respect to FIGS. 6 and 7 below. As shown in this cross-section, the microfuel cell 146 is "sandwiched" together to serve as a gas delivery structure for a fuel, for example hydrogen gas $H_2$, and for an oxidant (e.g., $O^2$). The microfuel cell 146 also serves as a "current collector". More particularly, the microfuel cell 146 contains an anode current collector 152A and a cathode current collector 152B, which can both be formed, for instance, from a graphite block with machine paths thereon (not shown) for directing the fuel or the oxidant. In this aspect, graphite cloths 156A,B are provided to allow for gas diffusion from the current collectors 152A,B to a centrally located proton exchange membrane 148 having catalyst films 158A,B formed on each side of the exchange membrane 148. In this example, platinum is used to form the catalyst films 158A,B.

Figure 3:
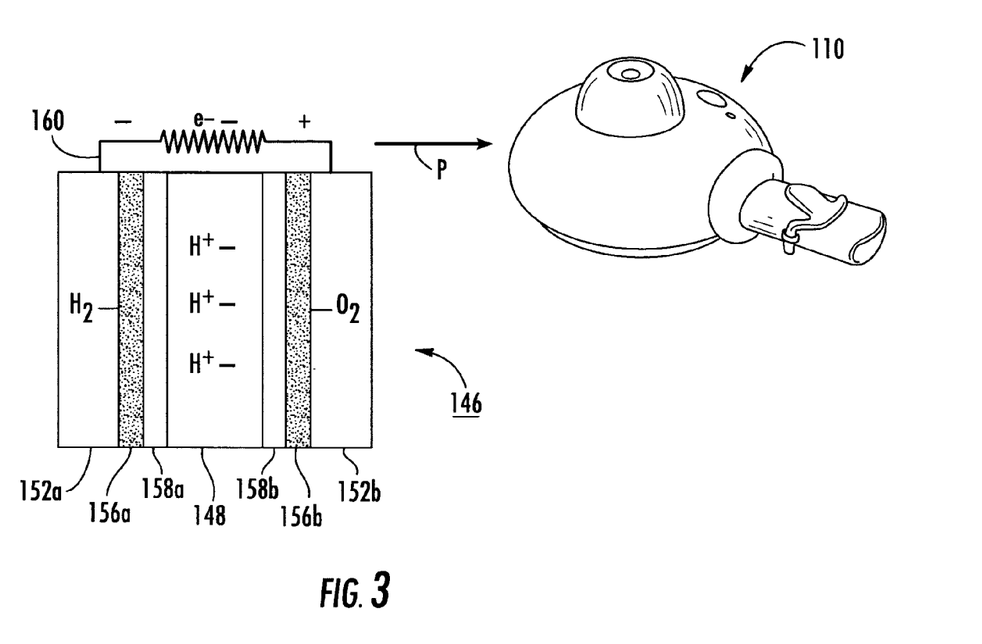
FIG. 3 is a schematic diagram of a micro fuel cell being used in a nebulizer according to an aspect of the invention.
Figure 4:
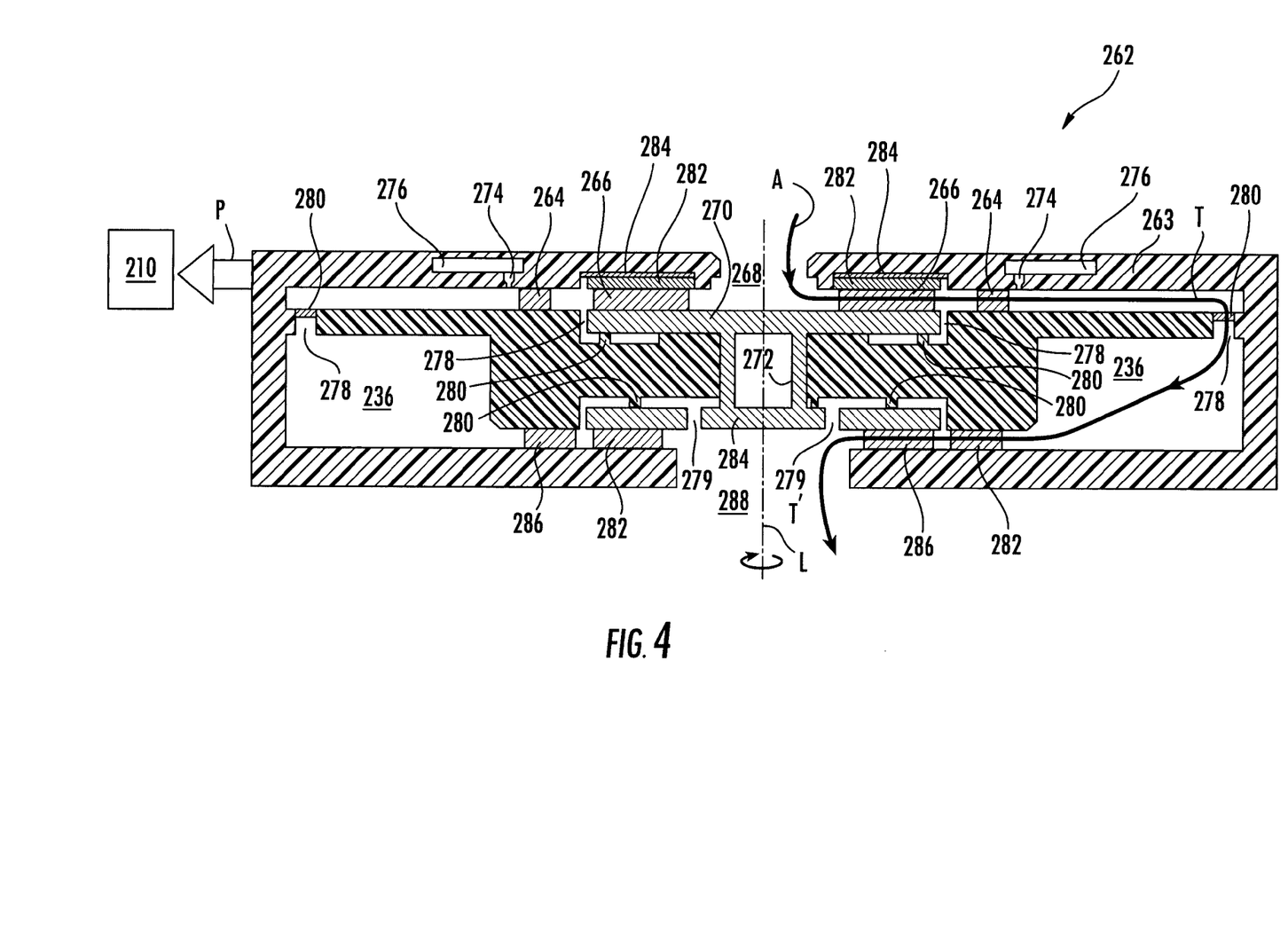
FIG. 4 is a cross sectional, elevational view of a micro power source for use in a gas-generating device in accordance with another aspect of the invention.
Figure 5:
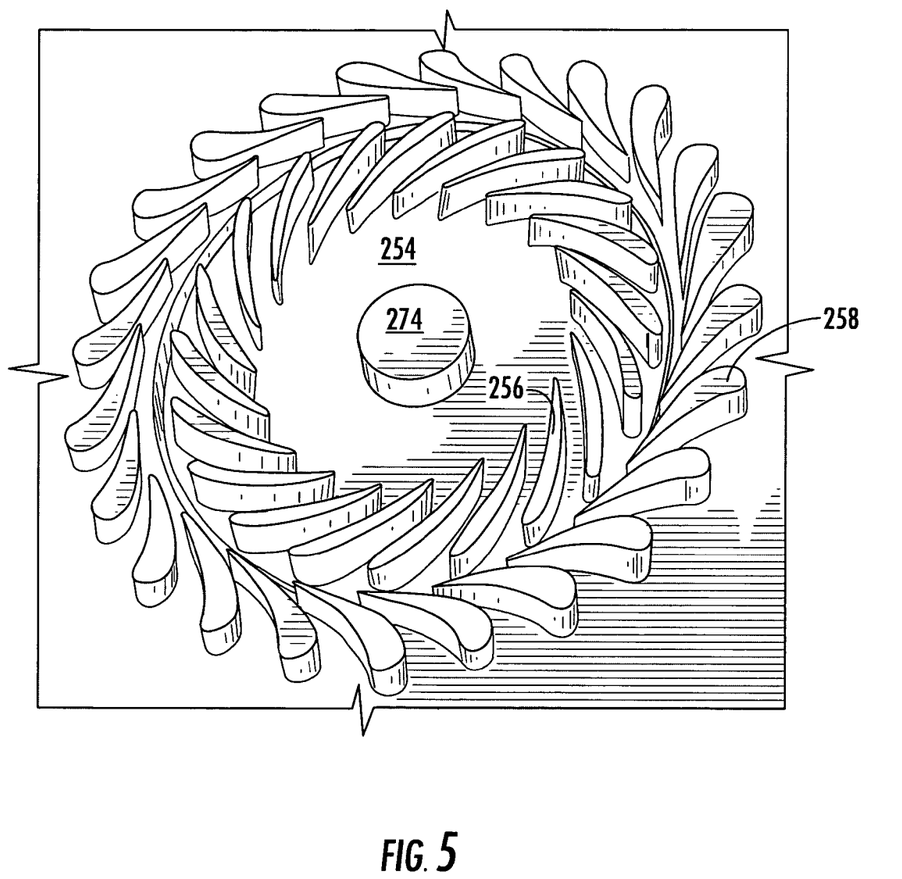
FIG. 5 is a top perspective view of a microturbine as used in the micro power source of FIG. 4.

As shown in FIG. 3, the hydrogen gas fuel $H_2$ moves through the machine paths in the anode current collector 152A, diffuses through the graphite cloth 156A and contacts the catalyst layer 158A. The catalyst strips electrons $e^-$ from the fuel $H_2$, and the electrons $e^-$ then travel through an external circuit 160. The remaining positive ions $H^+$ travel through the membrane 148 to the second catalyst layer 158B where they combine with oxygen ions formed when the free electrons $e^-$ travel from the circuit 160 and combine with the oxidant fed through the machine channels of the cathode current collector 152B. One byproduct of this process is electricity generated by the electron flow. Similar to the embodiment above, the electricity in this example is connected to and powers the nebulizer 110 via a power line P. Other byproducts of the process are heat and water. The heat can be recycled with the water to produce a water vapor. As described above with respect to FIG. 1, the water vapor can be combined with the aerosol A from the reservoir 14 for emission from the orifice 40.

Turning now to FIGS. 4 and 5, an alternative embodiment of a micro power source used to power a nebulizer 210, such as the nebulizer 10 described above, is a micro gas turbine engine or microengine 262, which generally includes a plurality of fixed diffuser vanes 264 disposed about a plurality of rotating compressor blades 266. In this example, the microgas turbine engine 262 is about 12 millimeters in diameter and about 3 millimeters in thickness and employs an air inlet 268 defining an area of about 1 $mm^2$. By way of exemplary operation, air A enters the microgas turbine engine 262 along a central line L defined through the inlet 268. As shown, the air A turns radially outward and is compressed in a centrifugal, planar microcompressor described below. Although only one air path A is apparent in FIG. 4 for clarity, the skilled artisan will appreciate that a continuous air path exists around a circumference of the microengine 262 and through its various components as more clearly shown in FIG. 5.

FIGS. 4 and 5 further show that the microcompressor includes a compressor rotor disk 270 that is approximately 4 millimeters in diameter in this example and has radial-flow rotor blades 266, which are about 250 micrometers in this example. As shown, the compressor rotor disk 270 is connected to a shaft 272 that is radially journaled for spinning, which in turn spins the compressor rotor disk 270 and the blades 266. Also shown, the plurality of stationary diffuser vanes 264 is located just beyond a radial periphery of the compressor rotor disk 270. Thus, the air A passing through the compressor rotor blades 266 exits the rotor with a large angular momentum that is removed by the vanes 264 in the diffuser and converted to a static pressurize.

More specifically, fuel (not shown) is injected at the discharge of the compressor rotor disk 270 by way of a fuel injector 274, which is formed of a circular array of, e.g., about 100-200 fuel-metering orifices on the microengine housing 263. As shown, the injected fuel mixes with the air A while flowing radially outward. The fuel injectors 274 are supplied by, e.g., an annular supply plenum 276 that is connected to an external fuel tank such as the fuel cartridge 50 described above.

The air-fuel mixture of FIG. 4 traverses a diffuser region and then turns (indicated by the letter T) through about 90° to axially traverse a periphery of small holes; i.e., the combustor inlet ports 278 that define flame holders provided in the region between the ports 278. A plurality of combustion igniters 280, e.g., resistive heaters controlled to the auto-ignition temperature of the air-fuel mixture, is located at a number of the combustion inlet ports 278 to initiate combustion of the air-fuel mixture. The ignited mixture axially enters an annular microcombustion chamber 236 where the mixture is fully combusted. In this example, the microcombustion chamber 236 is between about 2 millimeters-10 millimeters in annular height and between about 0.5 millimeters-5.5 millimeters-long measured axially.

FIGS. 4 and 5 further show that the expanding exhaust gases from the microcombustion chamber 280 are discharged radially inward through stationary turbine guide vanes 282 to a planar radial inflow microturbine rotor disk 284. The turbine rotor disk 284 diameter can be substantially similar to that of the compressor rotor disk 270. Like the microcompressor, the turbine rotor disk 284 includes axial blades 286 similar in height to those of the compressor rotor 270. As shown, the turbine disk 284 is connected by way of the journaled shaft 272 to the compressor disk 270 and thus rotationally drives the microcompressor in response to combustion gases exhausted through the microturbine blades that cause the turbine disks to spin. Specifically, as discussed above, the microturbine is exhausted radially inward where the exhaust gas then turns axially (indicated by the letter T') leading the microengine 262 through an exhaust nozzle 288. Thus, the turbine rotor disk 284 can operate as a microgenerator for driving power electronics via the power line P that in turn drives an electrical load such as the resistor 30 introduced above.

With reference now to FIG. 6, another embodiment of a gas-generating device 310 is shown according to another aspect of the invention. Many components of this embodiment are similar to the foregoing embodiments and reference is made to the above-described embodiments to provide a full and enabling description for like or similar components not expressly described with respect to FIG. 6. As shown in FIG. 6, the gas-producing device 310 is a steamer or humidifier, which broadly includes a body or housing 312 including a steam generation chamber 326 and a nozzle or outlet 316 for releasing steam S from the steam generation chamber 326. A micro power source 318 is employed by the gas-producing device 310 to generate the steam S. As shown, the housing 312 defines a compartment 320 for housing the micro power source 318. Also shown (in phantom) within the housing 312 are two reservoirs, a first reservoir 314A and a second reservoir 314B. The first reservoir 314A holds a liquid L, which can be water, medication, saline solution or the like as described with respect to the foregoing embodiments. The second reservoir 314B can hold a medication M or other additive including water for mixing with the liquid L of the first reservoir 314A in the steam generation chamber 326.

As FIG. 6 more particularly shows, the first reservoir 314A includes a conduit 334A, which is controlled by a control assembly 328. Likewise, the control assembly 328 controls a conduit 334B of the second reservoir 314B. In this aspect of the invention, an on/off mechanism or regulator 344 can be activated by a user to cause a measured quantity of the liquid L and/or the medicine M to be drawn from the first and second reservoirs 314A,B into the steam generation chamber 326 where the mixed liquid and medicine L,M, for instance, can be heated. In this example, a resistor 330 is connected to the micro power source 318, and the resistor 330 produces heat via an electrical current provided by the micro power source 318. The resistor 330 therefore heats the liquid L and the medication M to produce the steam S.

Figure 6:
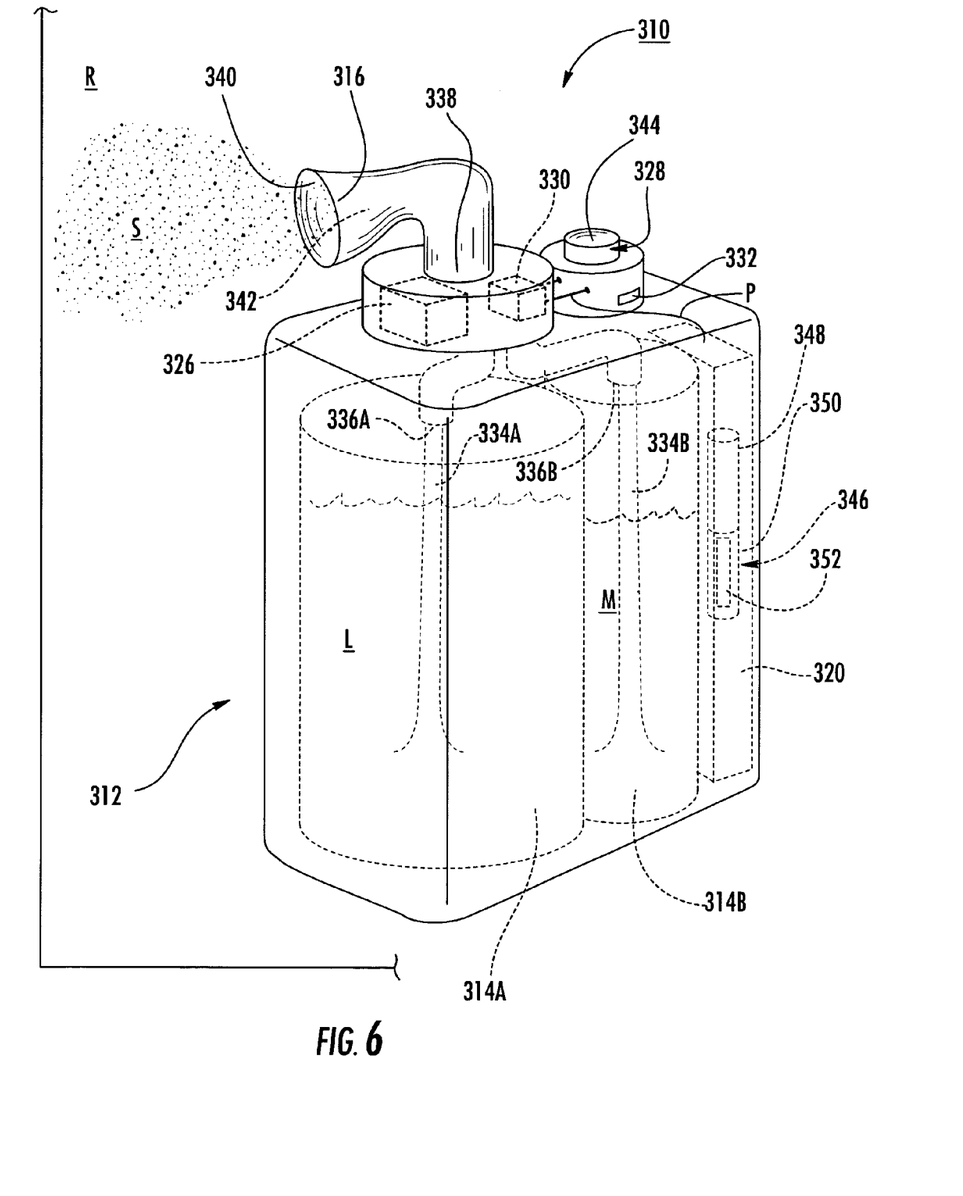
FIG. 6 is a perspective view of a humidifier powered by a micro power source according to another embodiment of the invention.

Also shown in the example of FIG. 6, the nozzle 316 has a first end 338 in communication with the chamber 326 to release the steam S into a room R through a second end or orifice 340 of the nozzle 316 via a passageway 342. An indicator 332 is also provided in this aspect of the invention to indicate to the user that the micro power source 318 is activated and/or that the liquid or medication levels L,M are low or depleted and need to be refilled through respective caps 336A and 336B on the first and second reservoirs 314A,B. Also shown in this example, the micro power source 318 is a fuel cell 346 including a combustion chamber 348 and a fuel cartridge 350, which is filled with fuel 352. As in the previous embodiment, when the fuel 352 is depleted, the indicator 332 can also indicate to the user that the fuel cartridge 350 must be refilled with fuel 352 or replaced in its entirety.

Figure 7:
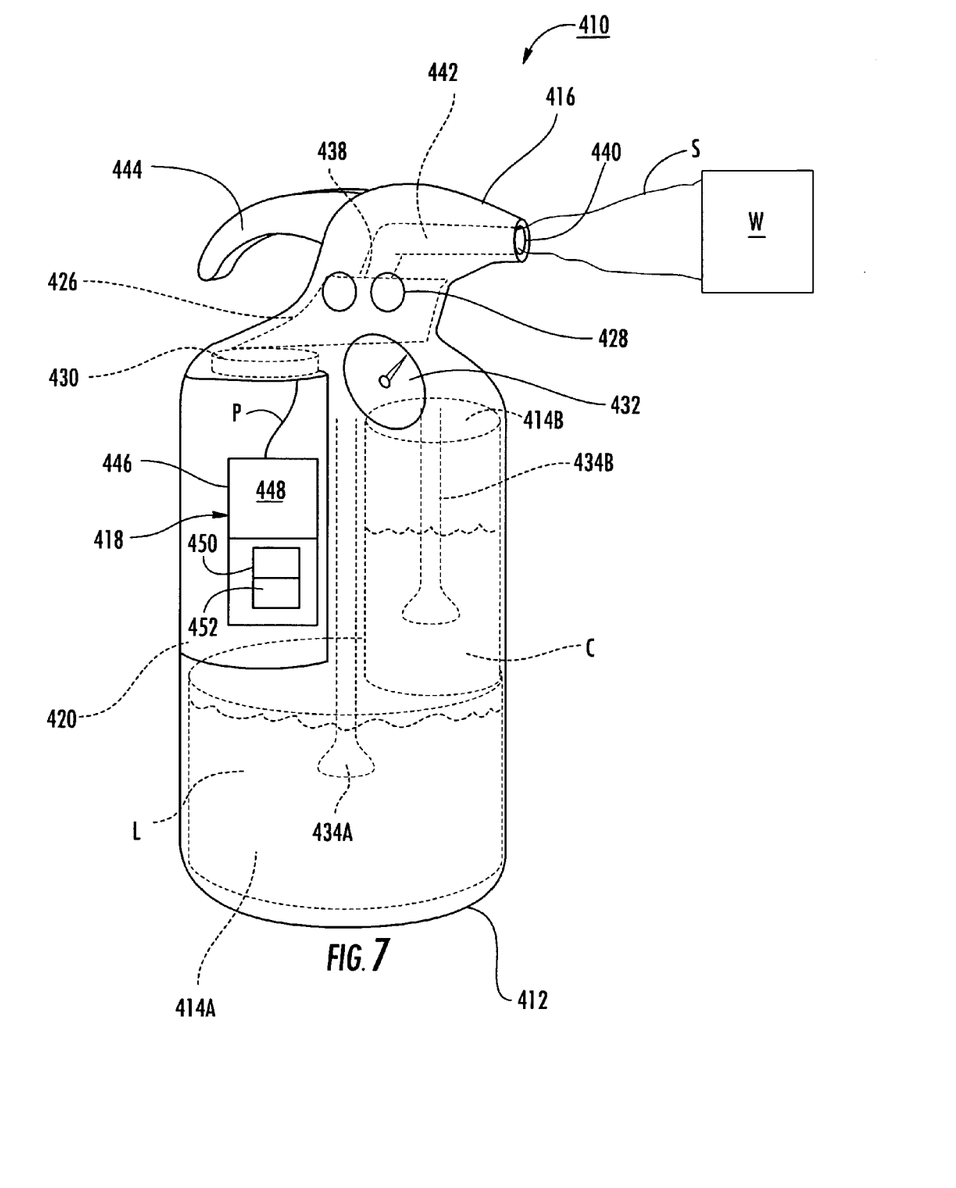
FIG. 7 is an elevational view of a steam-cleaning device powered by a micro power source according to another embodiment of the invention.

FIG. 7 shows another embodiment for a gas-generating device 410. In this example, the gas-generating device 410 broadly includes a body or housing 412 with a micro power source 418. Similar to the foregoing embodiment, the gas-generating device 410 produces steam S; however, in this example, the gas-generating device 412 is a steam-cleaning device. As shown, the gas-generating device 412 includes a compartment 420 defined in the housing 412 for holding the micro power source 418. A steam generation chamber 426 is also defined in the housing 412 for mixing with or heating a liquid L. Similar to the foregoing embodiment, a resistor 430 is connected to the micro power source 418 for heating the liquid L and/or the agent C. The liquid L can be heated by a resistor 430 or can be electrostatically charged or otherwise a property of the liquid L can be modified for cleaning various objects. A plurality of controls 428 is provided to adjust a temperature of the steam S, a delivery rate, or to add an agent C such as a cleaning agent.

More particularly, FIG. 7 shows a first and second reservoir 414A,B in the housing 412 for holding the liquid L and the agent C respectively. The first and second reservoirs 414A,B respectively include a first conduit 434A and a second conduit 434B that extract the liquid L or agent C into the steam generation chamber 426 upon activation of the controls 428 by a user. Once the liquid L and/or agent C are heated or otherwise affected by an electrical device 430, the user can activate a trigger 444 to deliver a charge of steam S onto a workpiece W to clean the workpiece W. As above, an indicator 432 such as a light, LED, or audible alarm, can be provided to indicate to the user that one or more of the liquid L, the cleaning agent C or the fuel 452 have been depleted and need to be replenished or replaced.

Figure 8:
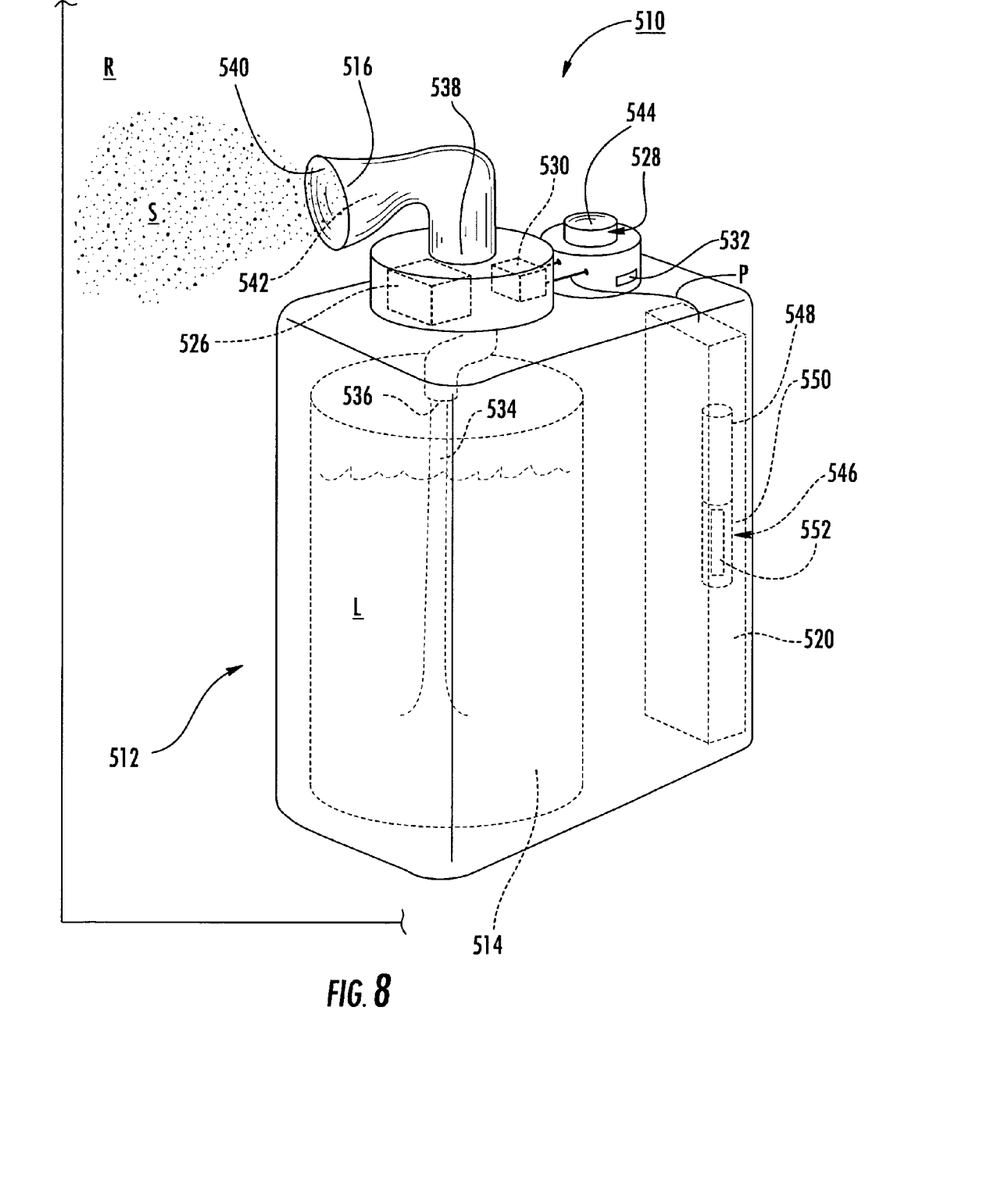
FIG. 8 is a perspective view of a portable device powered by a micro power source according to a further embodiment of the invention.

Turning now to FIG. 8, another embodiment of a gas-generating device 510 is shown according to another aspect of the invention. Many components of this embodiment are similar to the foregoing embodiments and reference is made to the above-described embodiments to provide a full and enabling description for like or similar components not expressly described in the following.

As shown in FIG. 8, the gas-producing device 510 broadly includes a body or housing 512 including a steam generation chamber 526 and a nozzle or outlet 516 for releasing steam S from the steam generation chamber 526. The gas-producing device 510 can be a portable or hand-held steamer or vaporizer, which can produce the steam S, an aerosol or the like and include a fragrance. The gas-producing device 510 can be held or worn by the user to breath the steam S via nose or mouth such as via a cup, a pendant, a hat or the like. Additionally, or alternatively, the gas-producing device 510 can be placed on a table surface or the like and used hands-free. By way of example but not of limitation, the gas-producing device 510 can be in the form of a cup such as the VAPOR SHOT! brand cup available from CNS, Inc. of Whippany, N.J.

With more particular reference to FIG. 8, a micro power source 518 is employed by the gas-producing device 510 to generate the steam S. The housing 512 defines a compartment 520 for housing the micro power source 518. Also shown (in phantom) within the housing 512 is a reservoir 514. The first reservoir 514 holds a liquid L, which can include water, medication, a fragrance, a medication, or a saline solution and the like and their combinations as described with respect to the foregoing embodiments.

As FIG. 8 shows, the reservoir 514 includes a conduit 534, which is controlled by a control assembly 528. In this aspect of the invention, an on/off mechanism or regulator 544 can be activated by a user to cause a measured quantity of the liquid L to be drawn from the reservoir 515 into the steam generation chamber 326 where the liquid can be heated. In this example, a resistor 530 is connected to the micro power source 518, and the resistor 530 produces heat via an electrical current provided by the micro power source 518. The resistor 530 therefore heats the liquid L to produce the steam S.

Also shown in the example of FIG. 8, the nozzle 516 has a first end 538 in communication with the chamber 526 to release the steam S into a room R through a second end or orifice 540 of the nozzle 516 via a passageway 542. An indicator 532 is also provided in this aspect of the invention to indicate to the user that the micro power source 518 is activated and/or that the liquid level L is low or depleted and needs to be refilled through a cap 536 on the reservoir 514. Also shown in this example, the micro power source 518 is a fuel cell 346 including a combustion chamber 548 and a fuel cartridge 550, which is filled with fuel 552. As in previous embodiments, when the fuel 552 is depleted, the indicator 532 can also indicate to the user that the fuel cartridge 550 must be refilled with fuel 552 or replaced in its entirety.

While preferred embodiments of the invention have been shown and described, those skilled in the art will recognize that other changes and modifications may be made to the foregoing embodiments without departing from the spirit and scope of the invention. For example, specific fuels described above and various devices and their shapes and materials and placement can be modified to suit particular applications. It is intended to claim all such changes and modifications as fall within the scope of the appended claims and their equivalents.

That which is claimed is:

1. A gas dispenser, comprising:
a reservoir being configured to hold a liquid;
a chamber in communication with the reservoir, the chamber being configured to receive the liquid;
a micro power source being configured to generate energy for conversion of the liquid disposed in the chamber to a gas;
a nozzle defining an orifice therethrough in selective communication with the chamber, the nozzle being configured for releasing the gas from the chamber through the orifice;
an electrical device in communication with the micro power source wherein the electrical device comprises an electrostatic charger, the electrostatic charger being configured to generate electrostatically charged droplets within the gas;
a delivery portion configured to release the gas to the user; and wherein the electrostatic charger is located adjacent to and in open communication with the delivery portion.

2. The gas dispenser as defined in claim 1, wherein the liquid is selected from the group consisting of a quantity of water, a quantity of medicine, a quantity of fragrance and combinations thereof.

3. The gas dispenser as defined in claim 1, wherein the micro power source is configured to generate about 0.2 W to about 200 W.

4. The gas dispenser as defined in claim 1, wherein the micro power source is a fuel cell having a fuel cartridge and a combustion chamber, the fuel cartridge being configured to hold a supply of fuel, the combustion chamber being configured to receive and combust the fuel to generate the energy.

5. The gas dispenser as defined in claim 4, wherein the supply of fuel is adapted for generating an electrochemical reaction to generate the energy.

6. The gas dispenser as defined in claim 4, wherein the fuel cartridge is configured to be refillable with a replacement supply of fuel.

7. The gas dispenser as defined in claim 4, wherein the fuel cartridge is a replaceable fuel cartridge.

8. The gas dispenser as defined in claim 1, wherein the micro power source is a microturbine engine including a plurality of diffuser vanes and a plurality of compressor blades, the plurality of compressor blades being configured for rotation about the diffuser vanes to generate the energy.

9. The gas dispenser as defined in claim 1, further comprising an actuator connected to the reservoir for controlling a quantity of the liquid delivered to the chamber.

10. The gas dispenser as defined in claim 9, wherein the quantity of the liquid delivered to the chamber is a dose of medicine.

11. The gas dispenser as defined in claim 1, further comprising a controller in communication with the micro power source, the controller being configured to activate the micro power source to generate the energy.

12. The gas dispenser as defined in claim 11, wherein the controller is a conductivity contact being configured to activate the micro power source by a user touch.

13. The gas dispenser as defined in claim 1, further comprising an electrical device in communication with the micro power source, the electrical device disposed proximate the chamber and configured for converting the liquid to the gas.

14. The gas dispenser as defined in claim 13, wherein the electrical device is a heating element, the heating element being configured to heat the liquid into the gas.

15. The gas dispenser as defined in claim 1 further comprising a regulator interposed between the chamber and the orifice, the regulator being configured to release the gas from the chamber through the orifice.

16. The gas dispenser as defined in claim 1, further comprising a membrane defining a plurality of holes therethrough, the membrane disposed proximate the chamber, the holes being configured to convert at least a portion of the liquid into an aerosol for release through the orifice.

17. A gas dispenser, comprising:
a first reservoir being configured to hold a first liquid;
a second reservoir being configured to hold a second liquid;
a chamber in communication with the first and the second reservoirs, the chamber being configured to receive the first and the second liquids;
a micro power source being configured to generate energy for conversion of at least one of the first and the second liquids disposed in the chamber into a gas;
a nozzle defining an orifice therethrough in selective communication with the chamber, the nozzle being configured for releasing the gas from the chamber through the orifice;
an electrical device in communication with the micro power source wherein the electrical device comprises an electrostatic charger, the electrostatic charger being configured to generate electrostatically charged droplets within the gas;
a delivery portion configured to release the gas to the user; and
wherein the electrostatic charger is located adjacent to and in open communication with the delivery portion.

18. The gas dispenser as defined in claim 17, wherein the first liquid is selected from the group consisting of a quantity of water, a quantity of fragrance and combinations thereof.

19. The gas dispenser as defined in claim 17, wherein the second liquid is selected from the group consisting of a quantity of water, a quantity of fragrance, a quantity of cleaning solution, a quantity of wax and combinations thereof.

20. The gas dispenser as defined in claim 17, wherein the micro power source is configured to generate about 0.2 W to about 200 W.

21. The gas dispenser as defined in claim 17, wherein the micro power source is a fuel cell having a fuel cartridge and a combustion chamber, the fuel cartridge being configured to hold a supply of fuel, the combustion chamber being configured to receive and combust the fuel to generate the energy.

22. The gas dispenser as defined in claim 21, wherein the supply of fuel is adapted for generating an electrochemical reaction to generate the energy.

23. The gas dispenser as defined in claim 21, wherein the fuel cartridge is configured to be refillable with a replacement supply of fuel.

24. The gas dispenser as defined in claim 21, wherein the fuel cartridge is a replaceable fuel cartridge.

25. The gas dispenser as defined in claim 17, wherein the micro power source is a microturbine engine being configured to generate the energy.

26. The gas dispenser as defined in claim 17, further comprising a controller in communication with the micro power source, the controller being configured to activate the micro power source to generate the energy.

27. The gas dispenser as defined in claim 26, wherein the controller is a conductivity contact being configured to activate the micro power source by a user touch.

28. The gas dispenser as defined in claim 17, further comprising an electrical device in communication with the micro power source, the electrical device disposed proximate the chamber and configured for converting at least one of the first and the second liquids into the gas.

29. The gas dispenser as defined in claim 28, wherein the electrical device is a heating element.

30. The gas dispenser as defined in claim 28, wherein the electrical device is an electrostatic charger, the electrostatic charger being configured to generate electrostatically charged droplets from at least one of the first and the second liquids.

31. The gas dispenser as defined in claim 17, further comprising a regulator interposed between the chamber and the orifice, the regulator being configured to release the gas from the chamber through the orifice.

32. A gas dispenser, comprising:
a reservoir being configured to hold a liquid;
a chamber in communication with the reservoir, the chamber being configured to receive a quantity of the liquid;
an actuator connected to the reservoir for dosing the quantity of the liquid to the chamber;
a micro power source being configured to generate energy for conversion of the liquid disposed in the chamber into an aerosol;

a nozzle defining an orifice therein, the nozzle in selective communication with the chamber, the nozzle being configured for releasing the aerosol from the chamber through the orifice;

an electrical device in communication with the micro power source wherein the electrical device comprises an electrostatic charger, the electrostatic charger being configured to generate electrostatically charged droplets in the aerosol;

a delivery portion configured to release the aerosol to the user; and wherein the electrostatic charger is located adjacent to and in open communication with the delivery portion.

33. The gas dispenser as defined in claim 32, wherein the liquid is selected from the group consisting of a quantity of water, a quantity of medicine, a quantity of flavorant and combinations thereof.

34. The gas dispenser as defined in claim 32, wherein the micro power source is configured to generate about 0.2 W to about 200 W.

35. The gas dispenser as defined in claim 32, wherein the micro power source is a fuel cell having a fuel cartridge and a combustion chamber, the fuel cartridge being configured to hold a supply of fuel, the combustion chamber being configured to receive and combust the fuel to generate the energy.

36. The gas dispenser as defined in claim 35, wherein the supply of fuel is adapted for generating an electrochemical reaction to generate the energy.

37. The gas dispenser as defined in claim 35, wherein the fuel cartridge is configured to be refillable with a replacement supply of fuel.

38. The gas dispenser as defined in claim 35, wherein the fuel cartridge is a replaceable fuel cartridge.

39. The gas dispenser as defined in claim 35, further comprising a controller in communication with the micro power source, the controller being configured to activate the micro power source to generate the energy.

40. The gas dispenser as defined in claim 39, wherein the controller is a conductivity contact being configured to activate the micro power source by a user touch.

41. The gas dispenser as defined in claim 35, further comprising an electrical device in communication with the micro power source, the electrical device disposed proximate the chamber and configured for converting the liquid into the aerosol.

42. The gas dispenser as defined in claim 41, wherein the electrical device is a heating element, the heating element being configured to convert at least a portion of the aerosol into steam.

43. The gas dispenser as defined in claim 35, further comprising a regulator interposed between the chamber and the orifice, the regulator being configured to release the gas from the chamber through the orifice.

44. The gas dispenser as defined in claim 35, further comprising a membrane defining a plurality of holes therethrough, the membrane disposed proximate the chamber, the holes being configured to convert at least a portion of the liquid into the aerosol for release through the orifice.

45. The gas dispenser as defined in claim 35, further comprising a mouthpiece disposed proximate the orifice, the mouthpiece being configured for a user to inhale the aerosol from the orifice into a mouth of the user.

46. The gas dispenser as defined in claim 45, wherein the mouthpiece is a mask being configured for placement over the mouth for the user to inhale the aerosol.

* * * * *